(12) United States Patent
Frenz

(10) Patent No.: US 10,220,256 B2
(45) Date of Patent: Mar. 5, 2019

(54) ATHLETIC PERFORMANCE BY TRACKING OBJECTS HIT OR THROWN AT AN ELECTRONIC DISPLAY

(71) Applicant: Fine Road Enterprises LLC, St. Louis, MO (US)

(72) Inventor: Thomas R. Frenz, St. Louis, MO (US)

(73) Assignee: SmartMitt, LLC, St. Louis, MO (US)

( * ) Notice: Subject to any disclaimer, the term of this patent is extended or adjusted under 35 U.S.C. 154(b) by 0 days.

(21) Appl. No.: 15/396,642

(22) Filed: Dec. 31, 2016

(65) Prior Publication Data

US 2018/0050233 A1 Feb. 22, 2018

Related U.S. Application Data

(60) Provisional application No. 62/376,332, filed on Aug. 17, 2016.

(51) Int. Cl.
| | | |
|---|---|---|
| *H04N 7/18* | (2006.01) | |
| *A63B 24/00* | (2006.01) | |
| *G06T 7/20* | (2017.01) | |
| *A63B 71/06* | (2006.01) | |
| *A63B 69/00* | (2006.01) | |

(52) U.S. Cl.
CPC ...... *A63B 24/0021* (2013.01); *A63B 69/0002* (2013.01); *A63B 71/0619* (2013.01); *G06T 7/20* (2013.01); *A63B 2024/0034* (2013.01); *A63B 2208/0204* (2013.01); *A63B 2220/16* (2013.01); *A63B 2220/806* (2013.01); *G06T 2207/10016* (2013.01); *G06T 2207/30224* (2013.01); *G06T 2207/30241* (2013.01)

(58) Field of Classification Search
CPC .............. A63B 2220/806; A63B 71/0605
USPC ........................................ 348/77, 157
See application file for complete search history.

(56) References Cited

U.S. PATENT DOCUMENTS

| | | |
|---|---|---|
| 5,419,549 A | 5/1995 | Galloway et al. |
| 5,553,846 A | 9/1996 | Frye et al. |
| 8,142,267 B2 | 3/2012 | Adams |
| 8,333,670 B2 | 12/2012 | Ono |
| 8,529,382 B2 | 9/2013 | Green et al. |
| 2015/0208044 A1* | 7/2015 | Jacobson ............... H04N 7/188 386/240 |

FOREIGN PATENT DOCUMENTS

| | | |
|---|---|---|
| KR | 200223323 Y1 | 5/2001 |
| KR | 101239527 B1 | 3/2013 |
| WO | WO 2014/104828 A2 | 7/2014 |

* cited by examiner

*Primary Examiner* — Andy Rao
(74) *Attorney, Agent, or Firm* — Hojka Qadeer, LLC; Cory L. Hojka

(57) ABSTRACT

The present disclosure relates to effective, efficient, and economical methods and systems for improving athletic performance by tracking objects typically thrown or hit by athletes. In particular, the present disclosure relates to a unique configuration of technology wherein an electronic display is located at or behind the target and one or more cameras are positioned to observe the target. Once an object is thrown or hit, one or more cameras may observe and track the object. Further, an electronic display may be used to provide targeting information to an athlete and also to determine the athlete's accuracy.

20 Claims, 23 Drawing Sheets

ATHLETIC PERFORMANCE BY TRACKING OBJECTS HIT OR THROWN AT AN ELECTRONIC DISPLAY

CROSS REFERENCE TO RELATED APPLICATIONS

This application claims the benefit of and priority to U.S. Provisional Patent Application Ser. No. 62/376,332, filed Aug. 17, 2016, the entirety of which is hereby incorporated herein by reference.

BACKGROUND

Field of the Invention

The present disclosure relates to methods and systems for improving athletic performance by tracking objects typically thrown or hit by athletes.

Description of the Related Art

Many sports require that an athlete repeatedly throw or hit an object to a target with a specific accuracy. For example, baseball requires that pitchers throw a baseball within a strike zone above a home plate. Further, a good pitcher in baseball should be able to throw a baseball to a specific area within the strike zone (e.g., lower right corner of the strike zone) that is optimal for striking out a player. Other sports besides baseball also have similar goals. For example, a good hockey player will be skilled at not just placing a puck in a goal, but also in targeting the puck to a specific area within the goal.

Currently, athletic training products on the market consist of static displays that only provide athletes with a fixed template to aim at, such as a vertical static display with colored grids showing different areas that the athlete can target. Rarely do such displays incorporate any form of feedback, though there are some products that measure speed of a thrown object using radar. However, these products do not provide a targeting system that can be easily adjusted, nor do they allow for electronically tracking and analyzing an athlete's performance. As a result, these training aids are highly limited in the feedback they can provide to athletes, coaches, parents, or others in understanding an athlete's individual performance. Further, they do not allow for easily comparing performance across athletes or according to factors deemed relevant to an athlete's performance, such as age or environmental conditions.

SUMMARY

The present disclosure is related to effective, efficient, and economical methods and systems for improving athletic performance by tracking objects typically thrown or hit by athletes. In particular, the present disclosure relates to a unique configuration of technology wherein an electronic display is located at or behind the target and one or more cameras are positioned to observe the target. Once an object is thrown or hit, one or more cameras may observe and track the object. Further, an electronic display may be used to provide targeting information to an athlete and also to determine the athlete's accuracy.

An example of a system for monitoring objects thrown or hit by an athlete is described herein. The system may comprise an electronic display, wherein the electronic display contains an arrangement of light-emitting devices for displaying targets to the athlete; one or more cameras, wherein at least one camera is positioned to observe the electronic display; and a computer coupled to the electronic display and the one or more cameras, wherein the computer uses video from the one or more cameras to determine relative to the electronic display where an object is thrown or hit.

A computer operable method is described for monitoring objects thrown or hit by an athlete. The method may comprise observing an electronic display, wherein the electronic display contains an arrangement of light-emitting devices for displaying targets to the athlete, via one or more cameras, wherein at least one camera is positioned to observe the electronic display; and using video from the one or more cameras to determine relative to the electronic display where an object is thrown or hit.

BRIEF DESCRIPTION OF THE DRAWINGS

FIG. 19 illustrates another example of multiple user records.

FIG. 24 illustrates another example of how a target data template may be constructed to form a game mode.

DETAILED DESCRIPTION OF ILLUSTRATED EMBODIMENTS

Although the invention will be described in connection with certain preferred embodiments, it should be understood that the invention is not limited to those particular embodiments. On the contrary, the invention is intended to cover all alternatives, modifications, and equivalent arrangements as may be included within the spirit and scope of the invention as defined by the appended claims.

Figure 1:
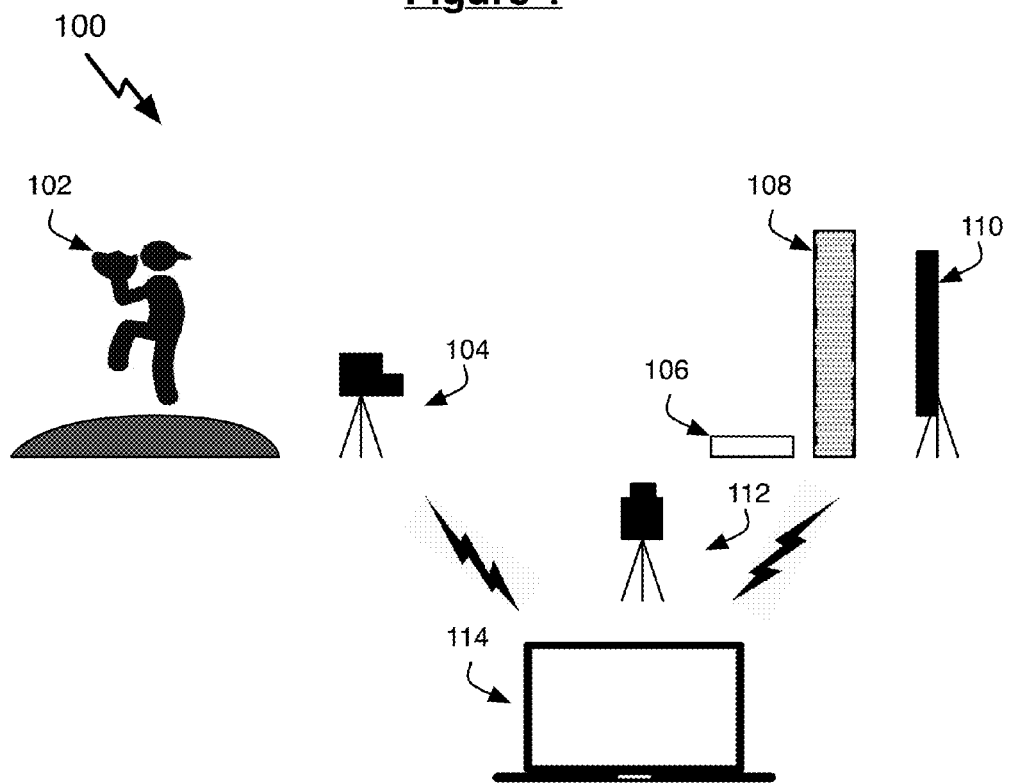
FIG. 1 illustrates an example of a system for tracking objects.

With respect to FIG. 1, an example of a System 100 for tracking objects is shown. In this embodiment, an Athlete 102 may be pitching from a baseball mound in the direction of Home Plate 106. Located behind Home Plate 106 may be a Catching Net 108, which may catch any pitch thrown near Home Plate 106. Located further behind Catching Net 108 may be a Target Display 110, which may display locations for the pitcher to throw at as described below. Between Athlete 102 and Target Display 110 may be Camera 104, which may be located on or near the line between a pitching mound and Home Plate 106 and may be oriented to observe Target Display 110. In addition, a Camera 112 may be placed to the side or at another position to observe the trajectory of a ball thrown by Athlete 102.

System 100 may also include a Computer 114, which may be connected to Camera 104, Target Display 110, and Camera 112. Computer 114 may instruct Target Display 110 to display a target showing areas that Athlete 102 should throw at. Computer 114 may then observe the performance of the athlete by tracking an object thrown toward Target Display 110, such as a baseball, via Camera 104. Based on the trajectory of the thrown object as recorded via Camera 104 or Camera 112, Computer 114 may determine a termination point where the trajectory of the object changes abruptly. Further, Computer 114 may determine the location of the termination point relative to visually distinct areas presented by Target Display 110. This may then be recorded into a data array by Computer 114, thereby allowing for the tracking of where objects have been repeatedly thrown by the athlete.

Figure 2:
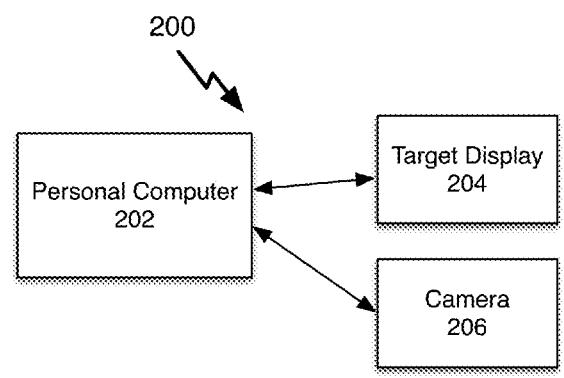
FIG. 2 illustrates another example of a system for tracking objects.

With respect to FIG. 2, an example of a System 200 for tracking objects is shown. System 200 may be comprised of a Personal Computer 202, a Target Display 204, and a Camera 206. System 200 is an example of a basic implementation of the systems described herein, which can be implemented using components described in FIG. 1. One of ordinary skill in the art will understand that, with respect to the hardware, custom or off-the-shelf components may be utilized. For example, Computer 200 may be a standard desktop or laptop running Windows, MacOS, Linux, etc. As a further example, Target Display 204 may comprise a standard television display, a screen on which images are projected from a video projector, or a custom arrangement as described below. As yet another example, Camera 206 may utilize any camera that has sufficient field of view and resolution to observe objects that are to be tracked and to observe visually distinct areas presented by Target Display 204.

Figure 3:
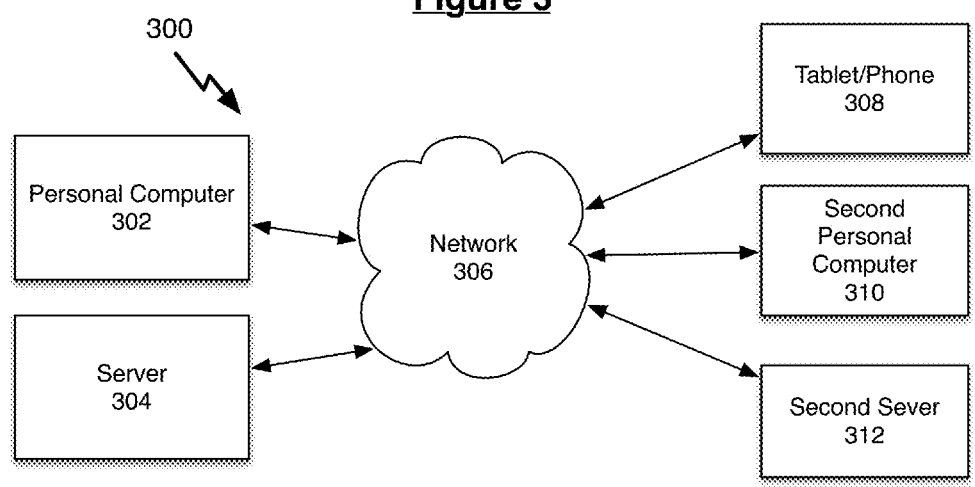
FIG. 3 illustrates another example of a system tracking objects.

With respect to FIG. 3, an example of a System 300 for tracking objects is shown. System 300 may include a Personal Computer 302. Personal Computer 302 may be connected to a Network 306 for exchanging data via network communications. Network 306 may be any type of computer network, such as the Internet, or other data communication network, such as a Bluetooth, Cellular, ZigBee, etc., that facilitates the exchange of electronic information. Via Network 306, Personal Computer may be able to upload or download data to or from Server 304 as described below. In addition, Network 306 may also facilitate the exchange of information between Personal Computer 302 or Server 304 with Tablet/Phone 308, Second Personal Computer 310, or Second Server 312. Personal Computer 302 may perform the same functions as Computer 114.

Figure 4:
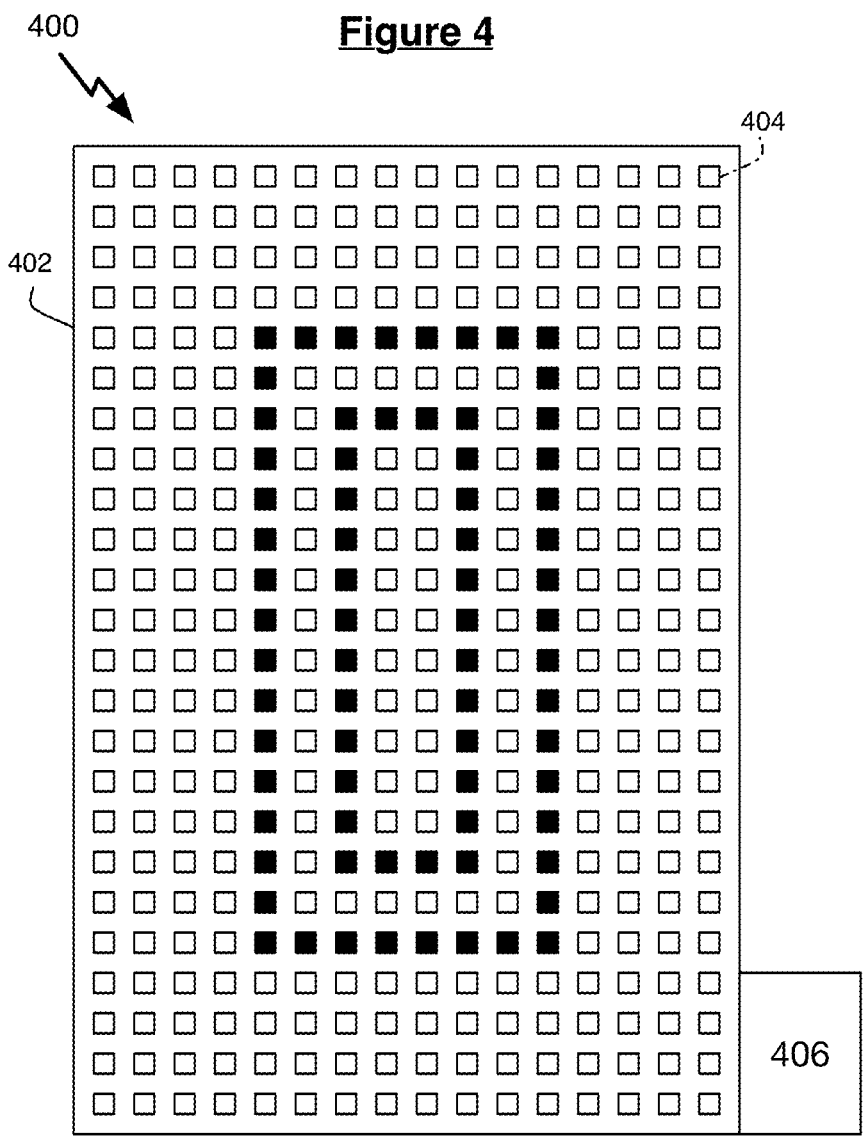
FIG. 4 illustrates an example of a custom target display.

With respect to FIG. 4, an example of a custom Target Display 400 is shown. Target Display 400 may consist of a Mounting Platform 402 attached to which is one or more Display Modules 404. For example, Mounting Platform 402 may consist of a rubber mat suspended vertically from a metal frame (or as another example it may be a metal frame constructed in the form of a grid-like vertical structure). Further, a 16×24 array of Display Modules 404 may be placed on Mounting Platform 402 as shown in FIG. 400. In other embodiments, various other size arrays (e.g., 24×24, 48×96) or other arrangements (e.g., circular, elliptical) may be employed. The one or more Display Modules 404 may then be connected to Display Component 406, which may allow Display Component 406 to control the state of each of Display Modules 404. In some embodiments, Display Modules 404 may be connected in sets to Display Component 406, which may allow Display Component 406 to control the state of each set of Display Modules 404.

Figure 5:
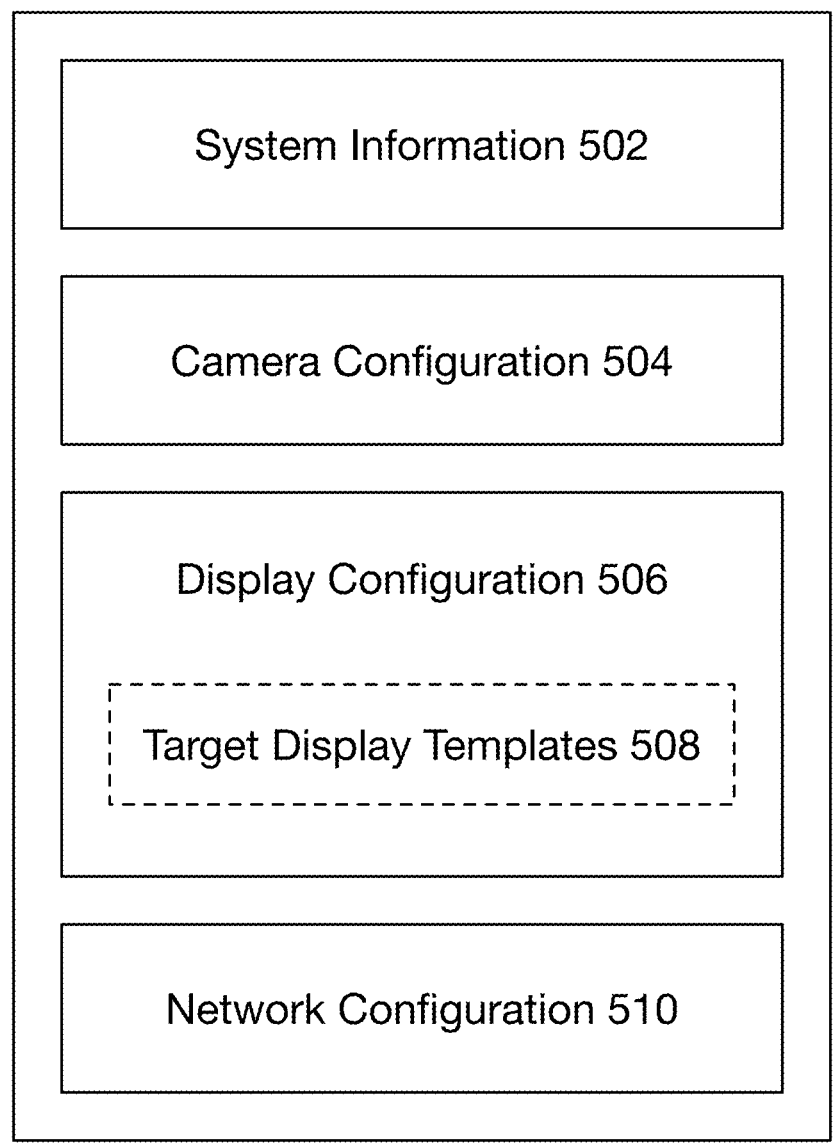
FIG. 5 illustrates an example of a system configuration.

With respect to FIG. 5, an example of System Configuration 500 is shown. System Information 502 may be used to store general information needed to configure the software components of the system, such as boot up parameters, location of essential files, etc. Camera Configuration 504 may be used to store information relating to initializing, configuring, and operating cameras attached to the system, such as Camera 104 shown in FIG. 1. Display Configuration 506 may be used to store information relating to initializing, configuring, and operating target displays attached to the system, such as Target Display 110. For example, Target Display Templates 508 may be created containing instructions of what is to be displayed on a Target Display 110. A Target Display Template 508 may specify a model number of a Target Display 400 and instructions for operating Display Modules 404 according to that model number. In some embodiments, a Target Display Template 508 may only contain patterns, which the system then interprets to fit a Target Display 110. For example, a Target Display Template 508 may contain an image, which the system may then interpolate, extrapolate, or otherwise adjust to operate within the display parameters of a specific Target Display 110. In addition, Display Configuration 506 may be used to store information relating to the display of information by the system on a computer display, such as the display of Computer 114. Network Configuration 510 may be used to store information relating to initializing, configuring, and operating network connections within the system, such as what entities (e.g., Personal Computer 302, Server 304, Tablet/Phone 308, Second Personal Computer 310, Second Server 312, etc.) can access information on the system.

Figure 6:
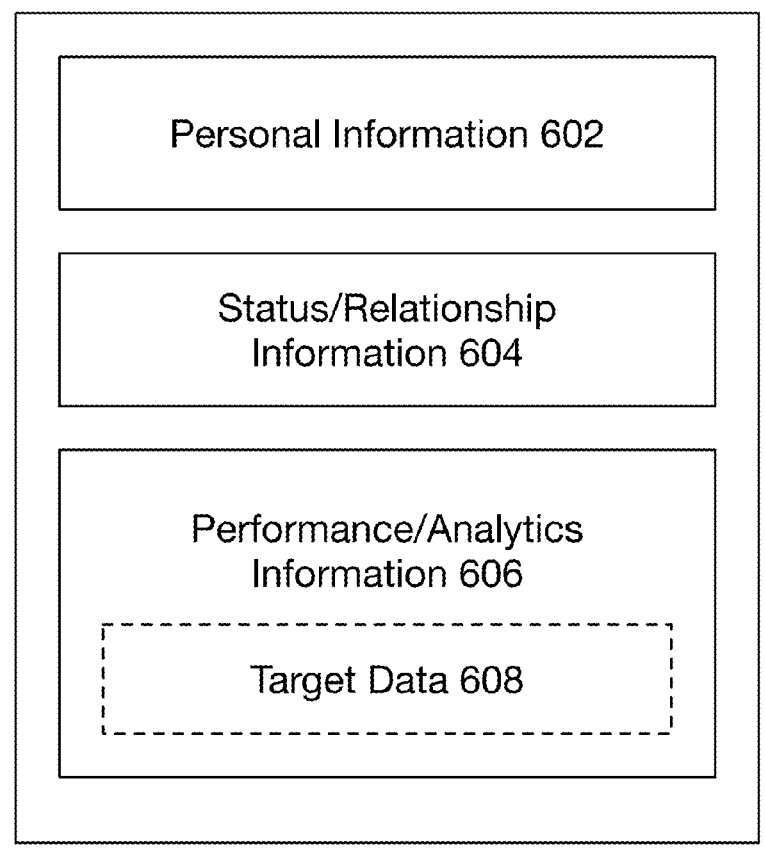
FIG. 6 illustrates an example of a user record.

With respect to FIG. 6, an example of a User Record 600 is shown. A User Record 600 may contain Personal Information 602 relating to a user, such as a user's name, nickname, mailing address, email address, age, gender, phone number, etc. User Record 600 may also contain Status/Relationship Information 604 relating to a user, such as specifying whether a user is an athlete, a coach, a parent/guardian, and may further contain relationship data to manage access between user records as described below.

User Record 600 may also contain Performance/Analytics Information 606, such as Target Data 608 corresponding to Target Display Templates 508. For example, an area around each Display Module 404 may be defined as a bin within a data array contained in Target Data 608. Each time that Computer 114 determines that an object hits within the area within a specific Display Module 404, it may update the bin within the data array of Target Data 608 associated with said area. In some embodiments, a bin within the data array of Target Data 608 may cover two or more Display Modules 404.

Target Data 608 may contain multiple arrays associated with Target Display 110. For example, a data array may only represent a particular range of time (e.g., corresponding to a practice session) or a data array may be the sum of other multiple data arrays. In addition, data arrays may contain addition information indicating the environment or other characteristics relevant to the data. For example, a pitching session may involve different targets displayed on Target Display 110, different weather conditions between sessions, different pitching stances, different lighting conditions (e.g., daylight vs. electric light), different geographic locations, etc. Accordingly, a data array contained within Target Data 608 may include any such information (e.g., athletic, environmental, geographic, or other factors) that is relevant to one or more object throwing or hitting sessions. In addition, once a data array is created in Target Data 608, it may be used as a template for other users. In some embodiments, a user may select to share such a data array with other users, while in other embodiments the system may determine what aspects of a data array in Target Data 608 may be shared.

Figure 7:
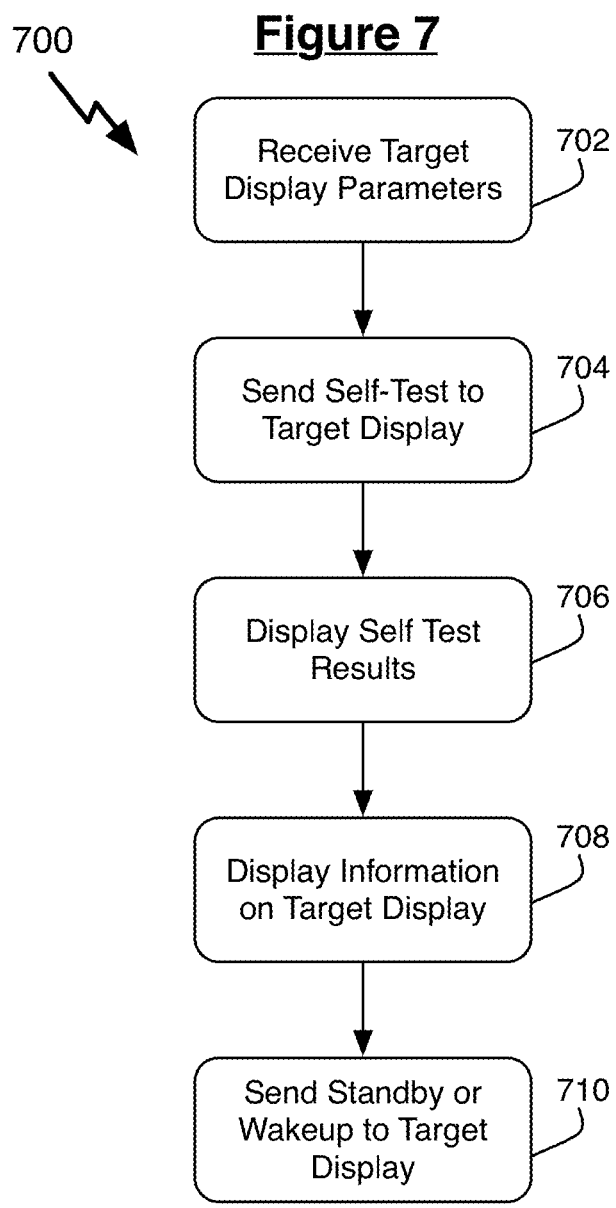
FIG. 7 illustrates an example of a method for controlling a target display using a computer.

With respect to FIG. 7, an example of a method 700 for controlling a Target Display 110 using a Computer 114 is shown. In Step 702, a Computer 114 may receive information specifying the capabilities of Target Display 110. For example, a model number specifying the capabilities of Target Display 110 may be selected by a user. Alternatively, Target Display 110 may provide such information (e.g., a model number or parameters) to Computer 114 upon connection of Target Display 110 to Computer 114. The Connection of Target Display 110 to Computer 114 may occur by wired or wireless communication. For example, Target Display 110 may use Wi-Fi, Bluetooth, or other protocols to communicate with Computer 114. Alternatively, well known wired methods such as Ethernet cables may be employed. In some instances, intermediate network devices, such as routers and hubs, may also be employed to connect Target Display 110 to Computer 114.

At Step 704, Computer 114 may instruct Target Display 110 to perform a self-test. For example, Target Display may methodically display a variety of different patterns to determine that all of its Display Modules 404 are functioning according to the expected capability of Target Display 110. As part of the self-test, Computer 114 may utilize a camera, such as Camera 104, to observe the self-test. For example, by observing the self-test via Camera 104, Computer 114 may confirm that all Display Modules 404 of the Target Display 110 are functioning properly and can be observed by Computer 114 via Camera 104.

At Step 706, the results of the self-test may be displayed to the user. If the self-test indicates a potential problem, it may provide instructions to the user. For example, Computer 114 may determine via the self-test that Camera 104 is too close to Target Display 110 and instruct the user to move Camera 104 or Target Display 110 further apart. As another example, Computer 114 may inform the user of a failure via the self-test to observe particular Display Modules 404 functioning properly and then may instruct the user to check for obstructions between Camera 104 and Target Display 110 that are blocking Camera 104 from observing said Display Modules 404.

At Step 708, Computer 114 may send display information to Target Display 110. For example, display information may specify the intensity and color that each Display Module 404 should exhibit. In some embodiments, the display information may contain further information relating to time-ordered sequences one or more Display Modules 404 should follow, thereby allowing for animated displays by Target Display 110. Particular examples of display information that may be shown by Target Display 110 are described below. In some embodiments, the display information may be obtained from Target Display Templates 510. In other embodiments, the display information may be obtained from Target Data 608.

At step 710, Computer 114 may send instructions to Target Display 110 to enter a standby mode or turn off. For example, Computer 114 may determine based on information received from a camera, such as Camera 104, that no objects have been thrown or hit for 15 minutes and send instructions to Target Display 110 to enter a standby mode. In some embodiments, Computer 114 may determine based on information received from a camera, such as Camera 104, that an object has been thrown or hit while Target Display 110 is in a standby mode and instruct Target Display 110 to leave standby mode. For example, Computer 114 via Camera 104 may observe a baseball entering its field of view and terminating on a net in front of Target Display 110.

Figure 8:
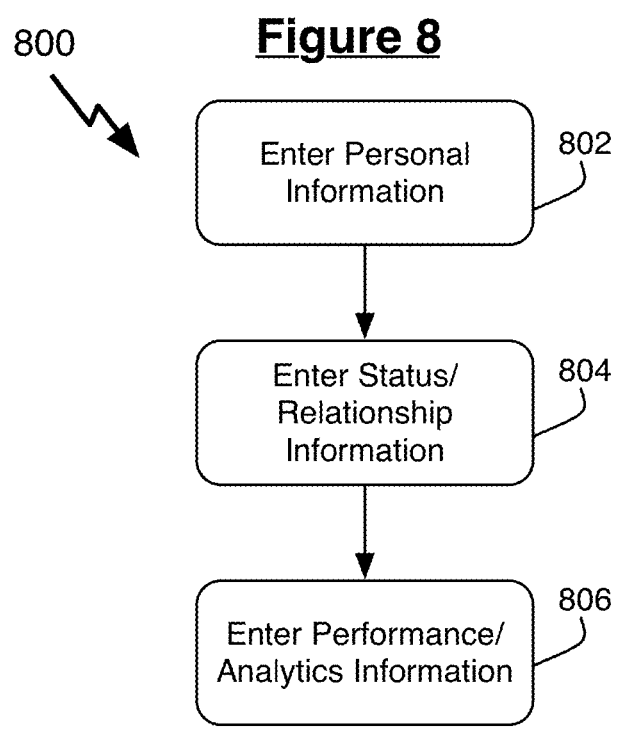
FIG. 8 illustrates a method for entering a user profile.

With respect to FIG. 8, a method 800 is shown for entering a user profile. At step 802, a user may enter Personal Information 602 into a User Record 600. At step 804, a user may enter Status/Relationship Information 604 into a User Record 600. For example, the user may specify that he or she is an athlete, coach, or parent. In addition, the user may also include information relating to characteristics of his or her status or relationship to other users. For example, if the user is an athlete, the user may specify the type of sport he or she plays, the position(s) he or she typically plays, whether he or she is right-handed or left-handed, and other athletic characteristics relevant to his or her status as an athlete. As another example, if the user is a coach, the user may specify the type of sport(s) he or she coaches, his or her title (e.g., assistant coach), and any particular expertise (e.g., pitching trainer).

In addition, users may specify relationships between each other. For example, a user may designate himself or herself as a coach to a set of users that are athletes, as a parent or guardian to a particular user, or as belonging to one or more organizations. In specifying such relationships, a user may be able to access information contained in User Records 600 based on such relationships. For example, a user who is a coach may be able to review the User Records 600 of users that are designated as athletes under the coach's supervision. The permissions to access such records based on relationships defined by users may be set by users themselves, a particular group of users having a specific status, by the system automatically, or a combination thereof.

At Step 806, a user may review Performance/Analytics Information 606 contained in a User Record 600. For example, a user may see how many balls were thrown on target and an index rating the performance of the athlete as a user. Further details about the Performance/Analytics Information 606 are provided below. In some embodiments, a user may also be able to edit the Performance/Analytics Information 606 contained in a User Record 600, such as instructing the record be reset or that analytics should ignore certain information, or to correct erroneous information stored by the system.

Figure 9:
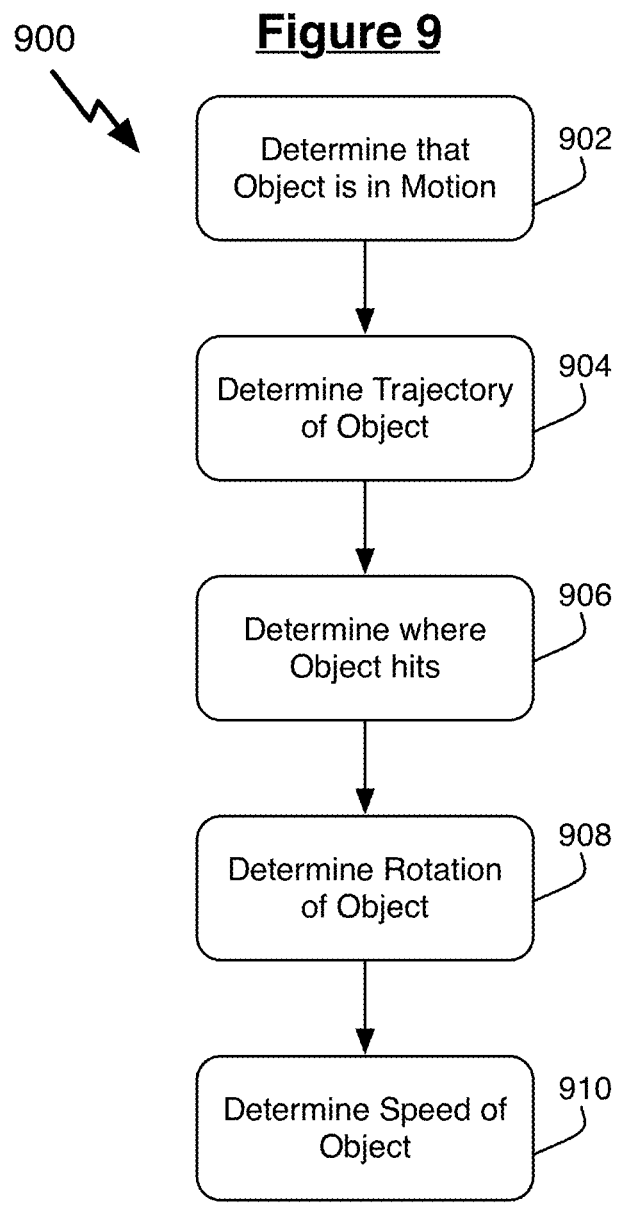
FIG. 9 illustrates an example of a method for calculating parameters relating to an object in motion.

With respect to FIG. 9, an example of a method 900 for calculating parameters relating to an object in motion is shown. At Step 902, Computer 114 may determine via one or more cameras, such as Camera 104, that an object is in motion. For example, Computer 114 may be instructed to look for a particular object in motion, such as a baseball, and upon observing said object entering the field of view of one or more cameras determine that an event, such as the pitching of a baseball may have occurred. Computer 114 may be instructed to observe for a wide variety of objects, such as baseballs, hockey pucks, footballs, soccer balls, etc. based on the expected way such an object will appear on a video screen (for example, a white round object of an initial size). In some embodiments, Computer 114 may determine the optimum parameters for detecting such an object based on an initialization routine (e.g., several baseballs are thrown and the system determines the best parameters identifying said object). In other embodiments, the system may attempt to track any object and may further determine if it is a valid object based on its trajectory.

At Step 904, Computer 114 may determine via one or more cameras the trajectory of the object. For example, based on each camera it may determine frame-by-frame the location of the object, and then create an array showing the position of the object over a period of time. In some embodiments, this array may then be superimposed over the display from each camera on Computer 114. In addition, when two or more cameras are used, Computer 114 may calculate a three-dimensional approximation of the trajectory of the object. This may then by displayed using methods known in the art to the user as a three-dimensional object on Computer 114 for manipulation by the user (e.g., rotating the 3D view).

At Step 906, Computer 114 may determine where an object hit. For example, it may determine based on the trajectory information calculated in step 904 where an object changed direction to denote a termination point. In addition, Computer 114 may then determine based on the termination point what is the closest Display Module 404 of a Target Display and use that to update a bin in a data array of Target Data 608. In some embodiments, the Target Display may show a visually distinct area based on color or intensity of a region. In such embodiments, Computer 114 may then determine based on the termination point what is the appropriate visually distinct area of the Target Display in which it resides.

At Step 908, Computer 114 may determine the rotation of the object. For example, an object may be marked with indicators allowing for one or more cameras to observe the rotation of the object. For example, a football may be painted half white and half orange and when the ball is thrown, Computer 114 may determine based on analysis of video recordings from one or more cameras the manner in which the object rotated (e.g., when the object goes from predominately white to orange and back again in a video feed from a side camera, Computer 114 may determine that this constitutes one rotation). In some embodiments, the markings may only be observable via spectrum not visible to the human eye, such as by using an infrared camera.

At step 910, Computer 114 may determine the speed of the object. For example, a user may specify the distance that the camera is located from a target. Based on that parameter and the known position and field of view of a camera relative to the target, Computer 114 may determine a distance between when an object enters the field of view and the target. Consequently, Computer 114 may calculate the speed of the object based on the number of video frames it takes for an object from entering the field of view of a camera to hit a target. As another example, when two or more cameras are used (such as a camera placed orthogonally to the trajectory of the object), Computer 114 may calculate the speed of the object based on trajectory information calculated in step 904. In some embodiments, markings in a physical environment may also be used to determine the speed of an object. For example, an overhead camera located above and in front of a target may observe the transition of an object over markings in the floor, thereby allowing for calculation of the object's speed based on such markings and the number of video frames required for the transition.

Figure 10:
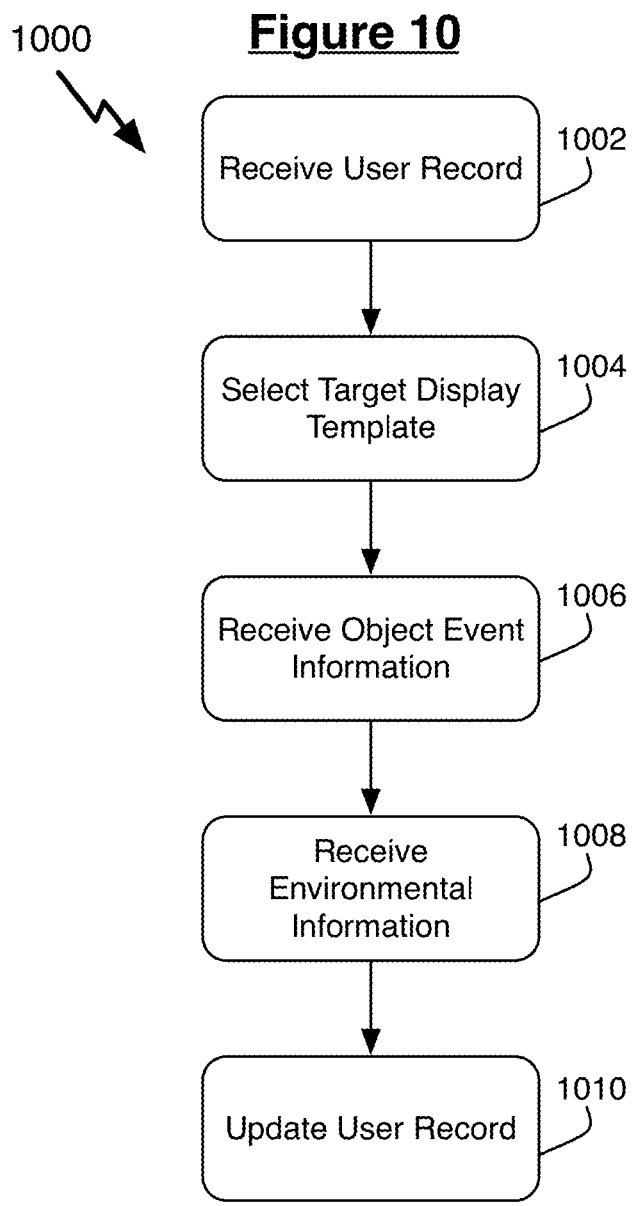
FIG. 10 illustrates an example of a method for processing an event or a series of events.

With respect to FIG. 10, an example of a method 1000 for processing an event or a series of events is shown. At step 1002, a Computer 114 may receive a User Record, such as a record associated with an athlete who is a baseball pitcher. At step 1004, a Computer 114 may select a Target Display Template for use with a Target Display 110. In some embodiments, the Target Display Template may be retrieved from the User Record itself, while in other embodiments the Target Display Template may be selected from Display Configuration 506. Based on the Target Display Template, Computer 114 may then proceed with the steps described in method 700 to set up a Target Display.

At step 1006, Computer 114 may receive information regarding an event recorded by cameras observing a thrown object, such as the throwing of an object at a target as described in method 900. For example, the athlete associated with the record may throw a baseball at the Target Display located behind a net, which may lead Computer 114 to receive information regarding the trajectory, rotation, speed, and hit location of the pitch.

At step 1008, Computer 114 may also receive information regarding environmental factors, such as light intensity, time of day, weather conditions, wind speed, location, etc. that a user has selected as relevant to the event recorded by cameras observing a thrown object.

At step 1010, Computer 114 may update the user record to include the information received in steps 1006 or 1008.

The above steps of method 1000 may be performed repeatedly for each object thrown or hit at the Target Display, thereby allowing for a cumulative record of performance to be recorded in a data array of Target Data 608 within the User Record.

Figure 11:
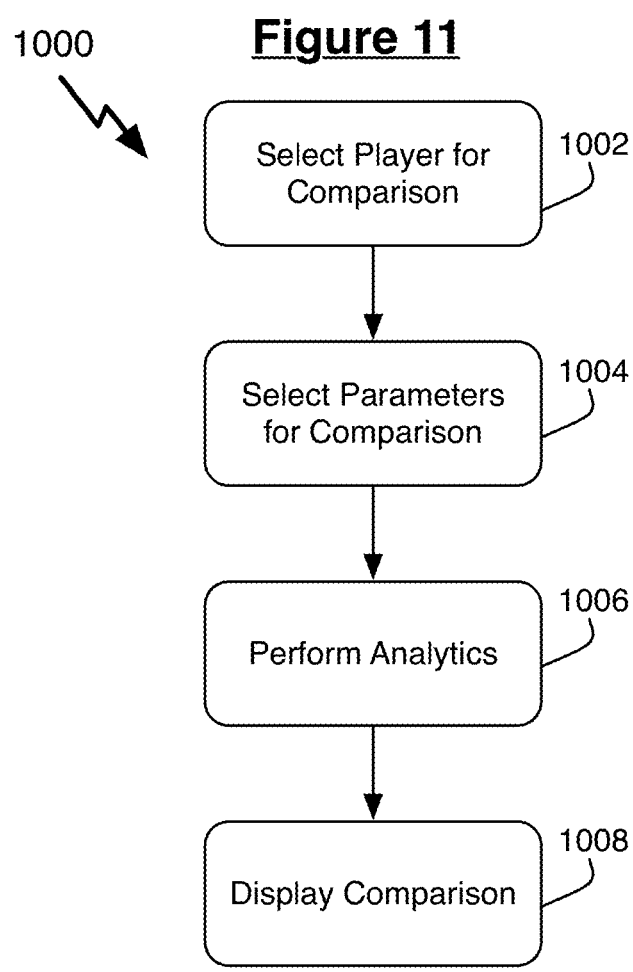
FIG. 11 illustrates an example of a method for comparing players according to their user records.

With respect to FIG. 11, an example of a method 1100 for comparing players according to their User Records is shown. At step 1102, a selection of a Player may be made for comparison, such as choosing a User Record via Computer 114. At step 1104, parameters may be chosen to determine how the comparison should be performed. For example, a comparison may be selected on the basis of age, throwing style, school, or other demographic, geographic, or athletic factors of interest. At step 1106, the comparison may be performed as requested. For example, Computer 114 may determine for each user record how they compare relative with respect to Target Display Templates that both users have utilized. At step 1108, the comparison may be displayed, such as on Computer 114.

While examples of the system herein are primarily described with respect to Computer 114, the functionality of Computer 114 may be implemented by other components, such as Server 304, Tablet/Phone 308, Second Personal Computer 310, or Second Server 312. In some embodiments, the functionality may be distributed across several such components or may be performed by a cloud-computing environment.

Figure 12:
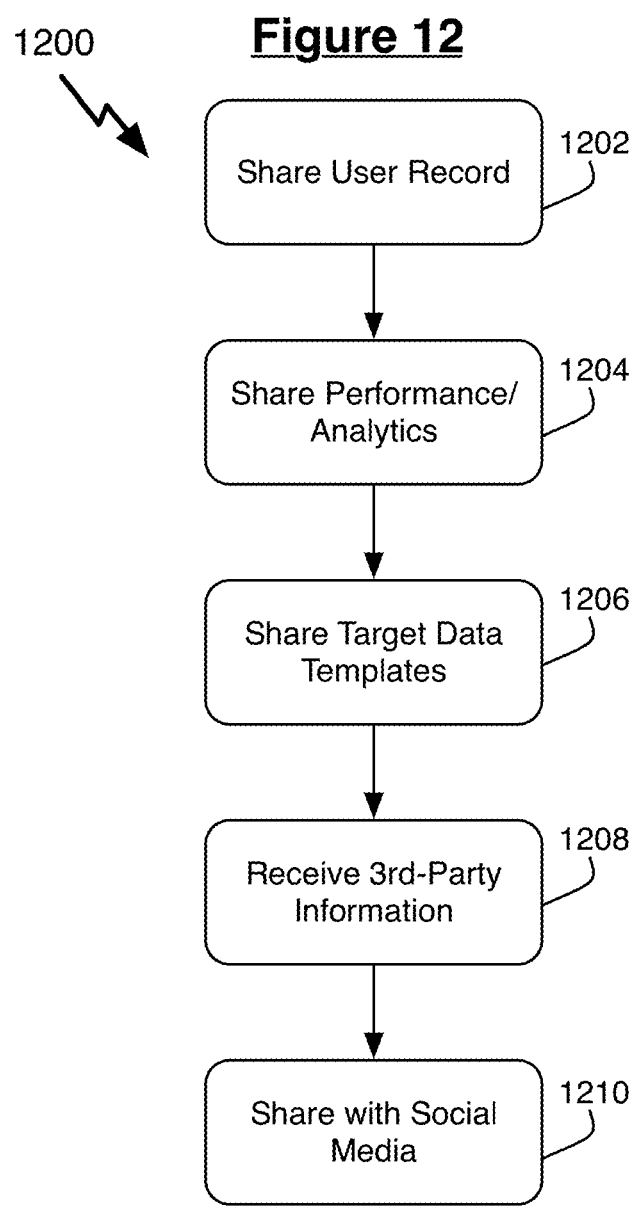
FIG. 12 illustrates an example of the network functionality of the system.

With respect to FIG. 12, an example of the network functionality of the system is described. To help illustrate this example, Personal Computer 302 may be a computer being used to operate the system on a baseball field, Server 304 is a server coupled to maintain a copy of the records on Personal Computer 302 that may have a more reliable Internet connection, and Tablet/Phone 308, Second Personal Computer 310, and Second Server 312 are in the possession of third-parties.

At step 1202, a request may be made to share a user record, such as a parent/guardian using his or her Tablet/Phone 308 to check on the performance of an athlete. As another example, a Little League may wish to gather comprehensive records of pitching performance for statistical evaluation using Second Server 312. Further, after performing such statistical evaluation, Second Server 312 may share its results with the system so as to enhance the system's performance/analytics information. For instance, rankings may be established based on the collected athletic performance that may then be incorporated by the system when analyzing an athlete's performance (e.g., a hit/miss ratio of 25% is a "Greenhorn", while a hit/miss ratio of 52% is a "Marksman"). In such embodiments, the system or a particular user may determine whether the person or device is authorized to access such records and also what information may be shared.

At step 1204, a request may be made to share only performance/analytics information. For example, this may be used in embodiments where access to any other portion of a user record is prohibited by child privacy laws or regulations. In such embodiments, the system or a particular user may determine whether the person or device is authorized to access such records and also what information may be shared.

At step 1206, a request may be made to share Target Data Templates. For example, coaches or instructors may wish to share Target Data Templates they have created with other coaches or instructors. Alternatively, users may wish to download Target Data Templates representing particular players they wish to compete against. For example, a user may wish to download Target Data Templates corresponding to a professional athletic team and simulate a game against them in Game Mode as described below. In such embodiments, the system or a particular user may determine whether the person or device is authorized to access such records and also what information may be shared.

At step 1208, a request may be made to Third Party services for information to include in User Records. For example, a request may be made for weather data, location data, etc. to include in a Target Data Record.

At step 1210, the system may be used to share information with social media. For example, the system may be configured to generate messages regarding athletic performance for social media (e.g., "Matty pitched like a Marksman in today's session!"). Templates for messages may be stored in System Information 502. Rules for determining how or when to generate such messages may be stored in System Information 502 or in individual User Records. In some embodiments, a user may use such templates and rules to generate and post such messages. In further embodiments, the system may use such templates and rules to generate and post such messages automatically.

Figure 13:
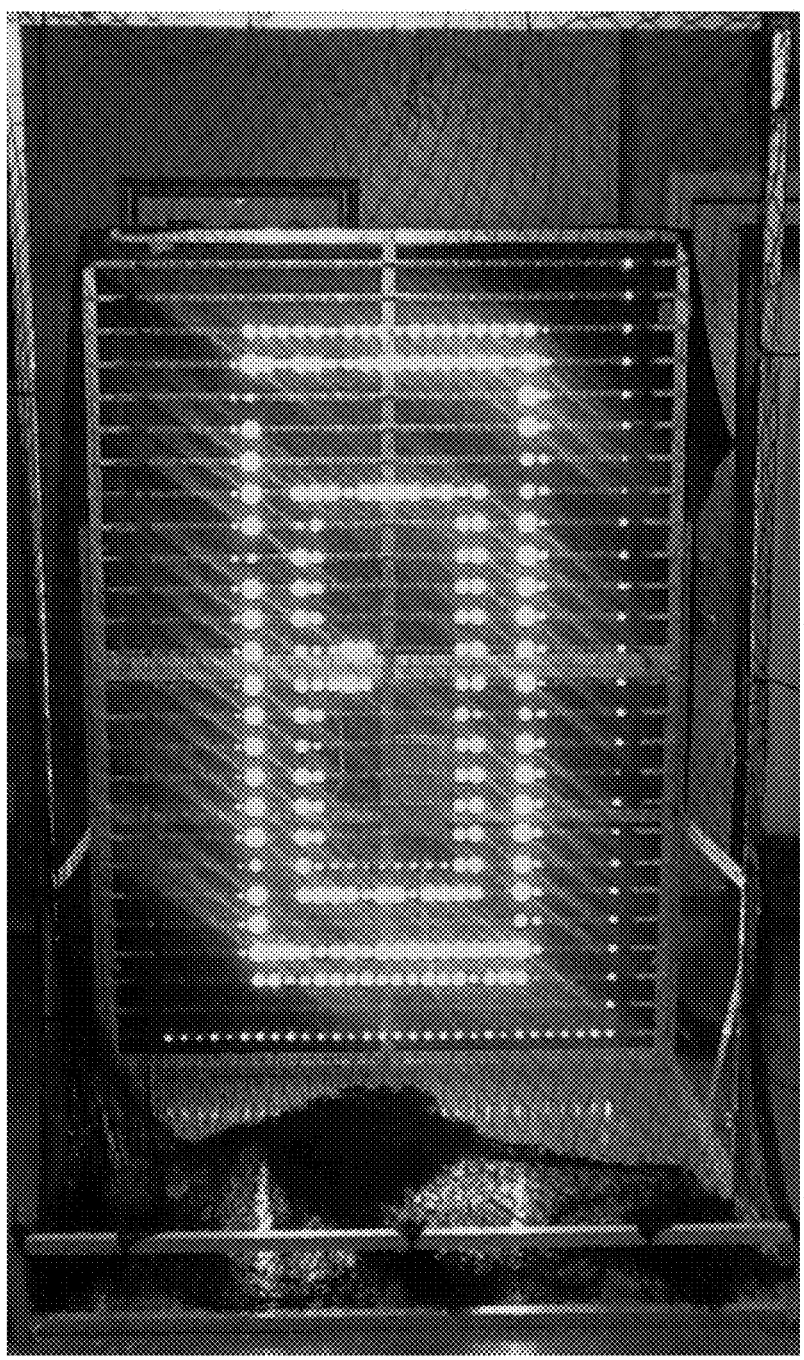
FIG. 13 illustrates an example of a target display.

With respect to FIG. 13, an example of a Target Display is shown. In this embodiment, LEDs are suspended on a vertical metal frame. The metal frame is composed of four sections, allowing for convenient disassembly and storage. Each LED shown in this example may be controlled separately in terms of light intensity and color by a computer. Further shown within FIG. 12 for exemplary purposes is a Target Data Template, which is being used to show the strike zone above a plate and within that a preferred target area for a pitcher.

Figure 14:
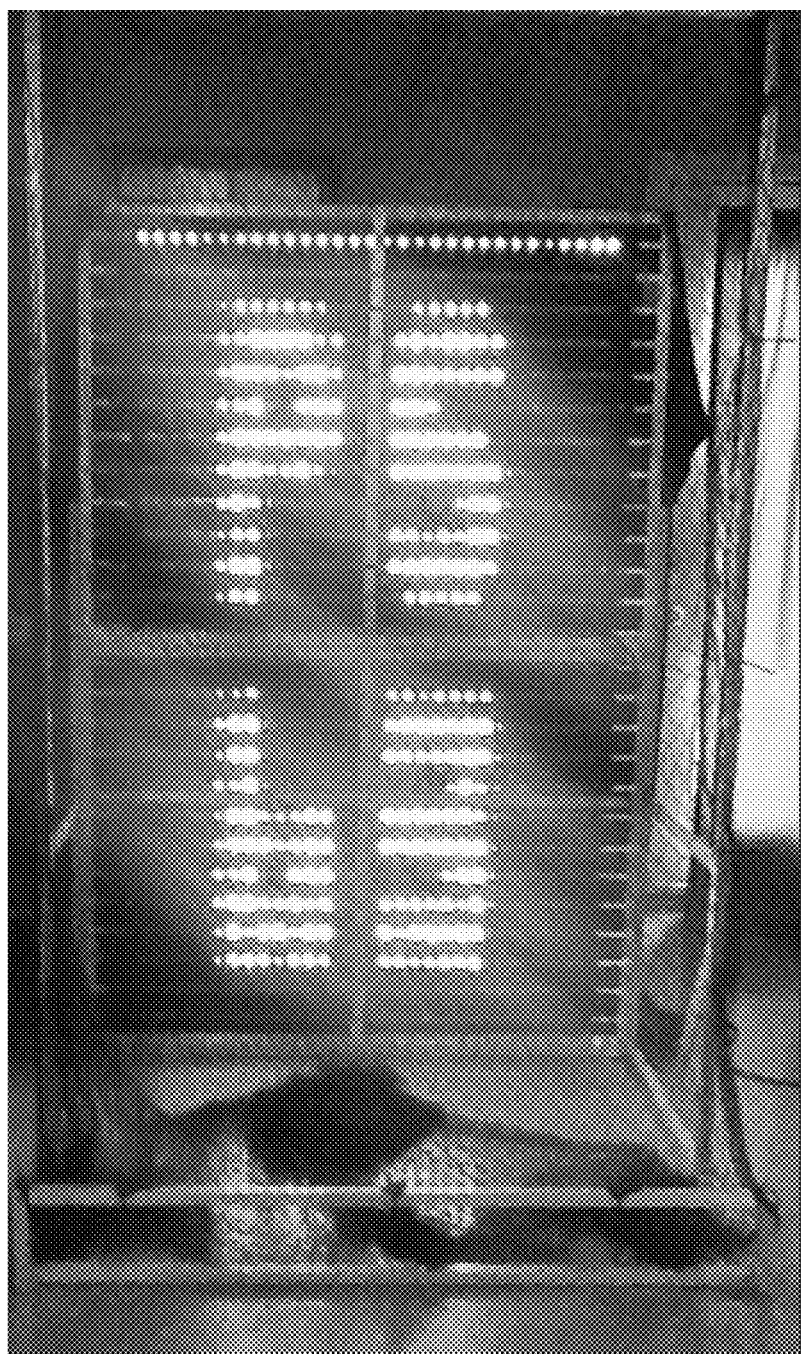
FIG. 14 illustrates another example of a target display.

With respect to FIG. 14, another example of the Target Display is shown. In this embodiment, the Target Display is showing that the last pitch was determined to have a speed of 63 MPH.

Figure 15:
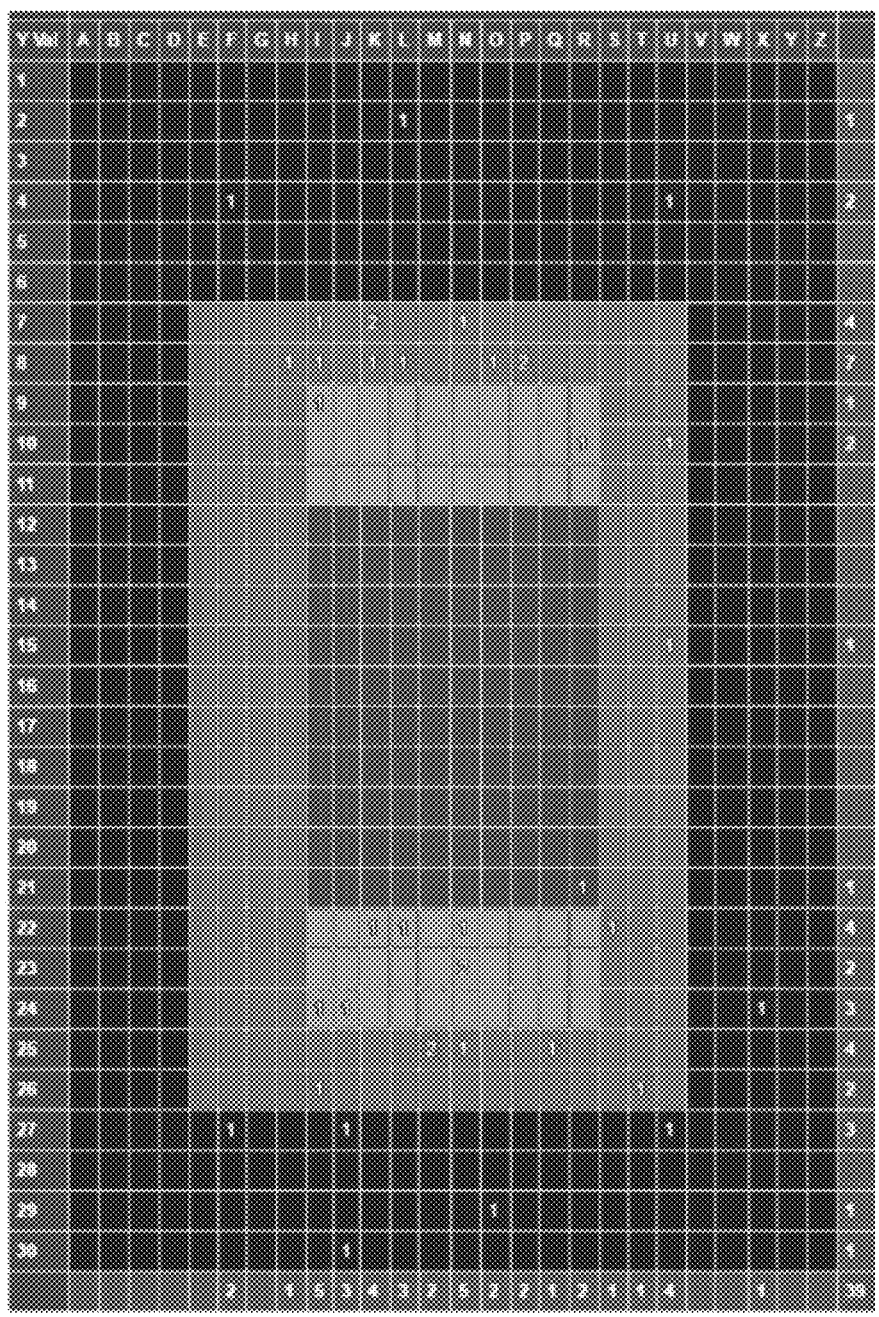
FIG. 15 illustrates an example of target data.

With respect to FIG. 15, an example of a Target Data 608 is shown. As shown, the Target Data 608 is based on a Target Display Template with five visually unique areas (ball zone, outer strike zone, and upper/middle/lower target zones within the outer strike zone). Further, Target Data 608 has been updated to show where termination points were determined to have occurred in relationship to the Target Display Template. For example, only one hit was recorded in the lower right portion of the inner/middle strike zone. As seen in FIG. 13, Target Data 608 may also include a summary along a horizontal line for each row of the data array. In other embodiments, Target Data 608 may include other similar summaries, such as on a vertical line for each row of the data array.

Figure 16:
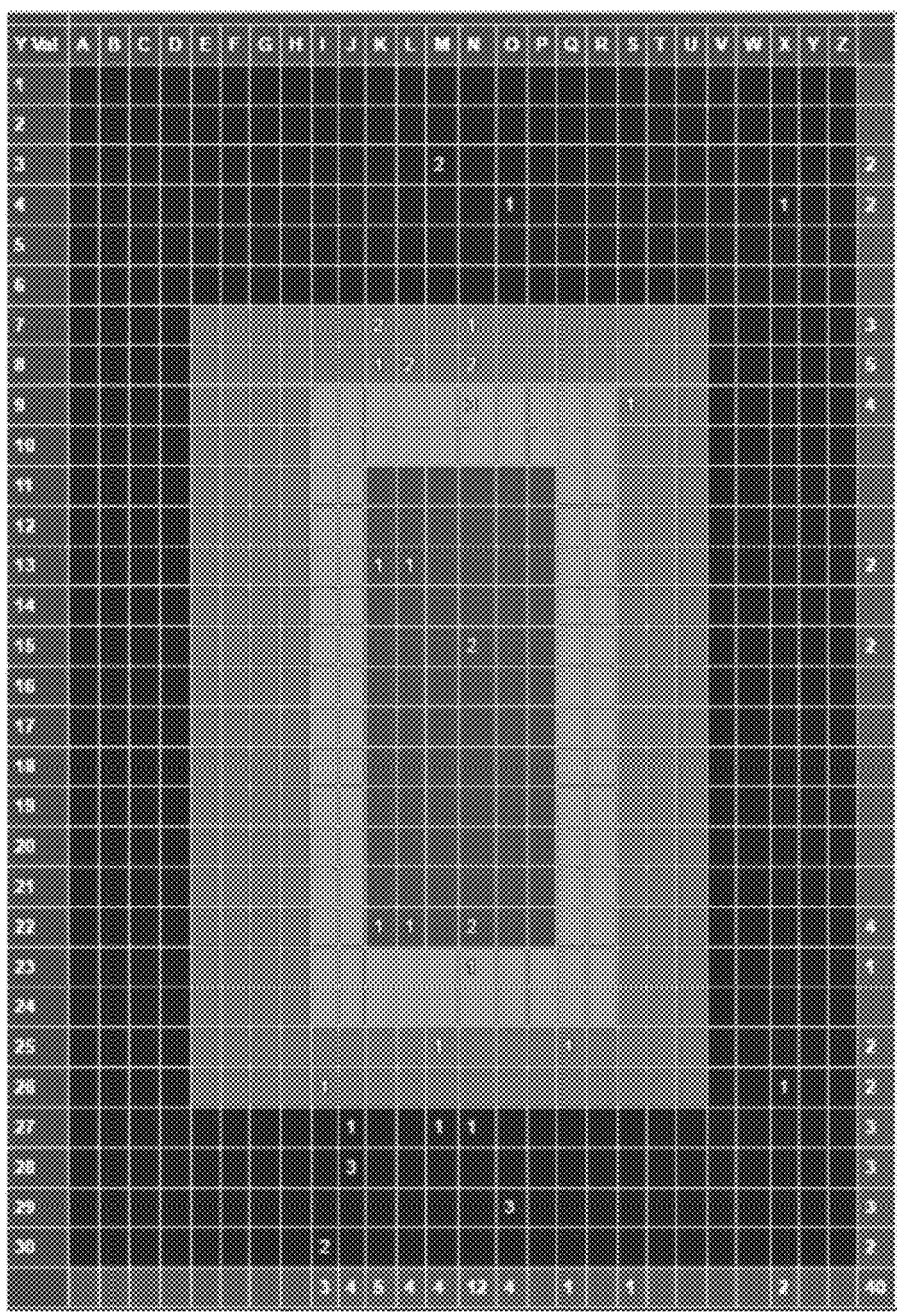
FIG. 16 illustrates another example of target data.

With respect to FIG. 16, another example of a Target Data 608 is shown. As shown, the Target Data 608 is based on a Target Display Template with four visually unique areas (ball zone, outer strike zone, middle strike zone, and inner strike zone).

Figure 17:
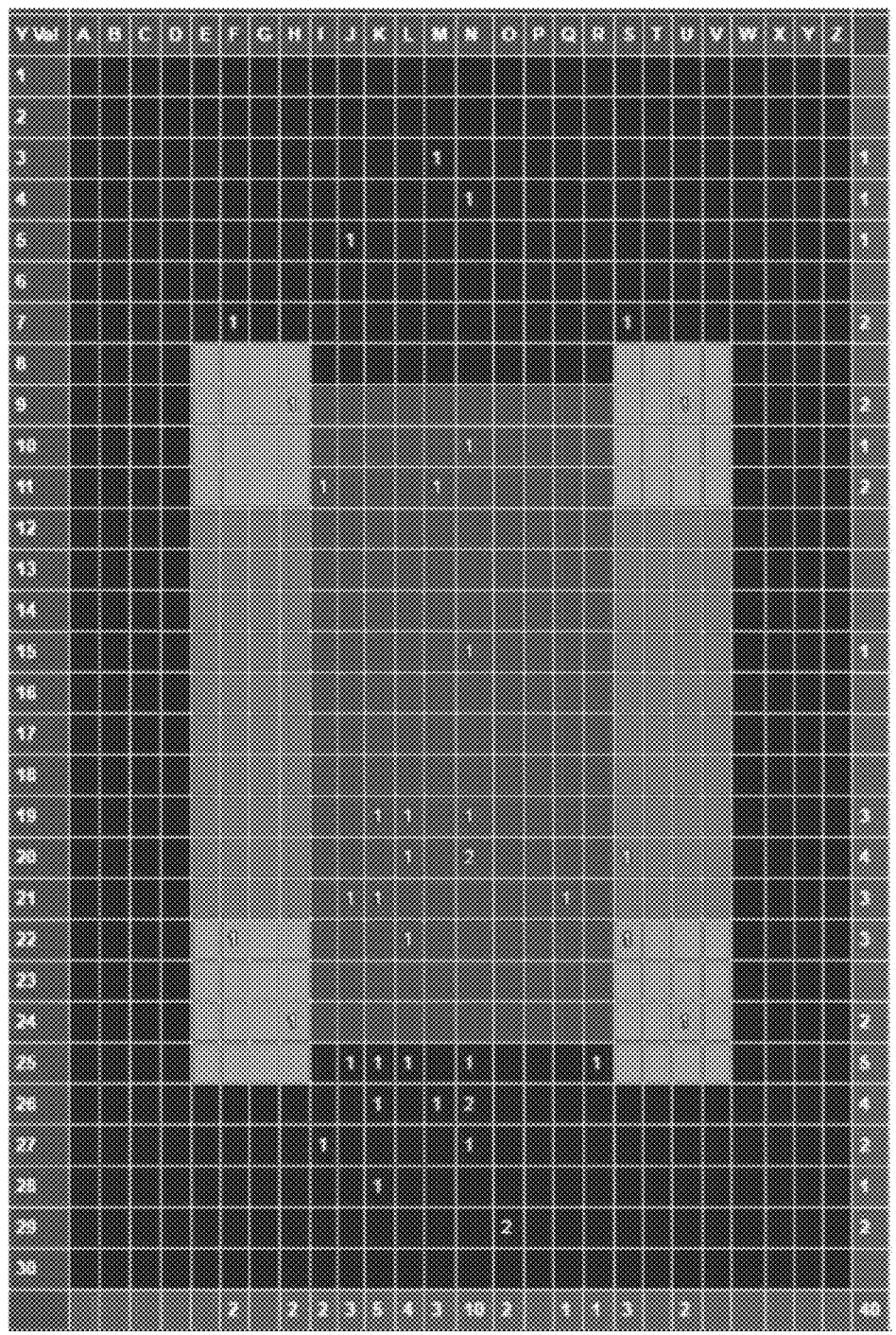
FIG. 17 illustrates another example of target data.

With respect to FIG. 17, another example of a Target Data 608 is shown. As shown, the Target Data 608 is based on a Target Display Template with eight visually unique areas. Though not shown in FIG. 17, each of these regions may be color coded to represent how they appear on a Target Display. In this example, the purpose of such a Target Display Template may be to teach how to throw to the corners of the strike zone. Accordingly, the area outside of the strike zones may be designated black (to indicate no light or color to be shown by the Target Display in those areas). The innermost strike zone area may be designated red (to indicate a red color to be shown by the Target Display in those areas), thereby discouraging aiming at that location. The corner strike zones may be designated green (to indicate a green color to be shown by the Target Display in those areas), thereby encouraging aiming at that location. Finally, the two vertical strike zone areas between the strike zone corners may be designated yellow (to indicate a yellow color to be shown by the Target Display in those areas), thereby showing that aiming at that location is acceptable.

Figure 18:
FIG. 18 illustrates an example of multiple user records.
Figure 19:
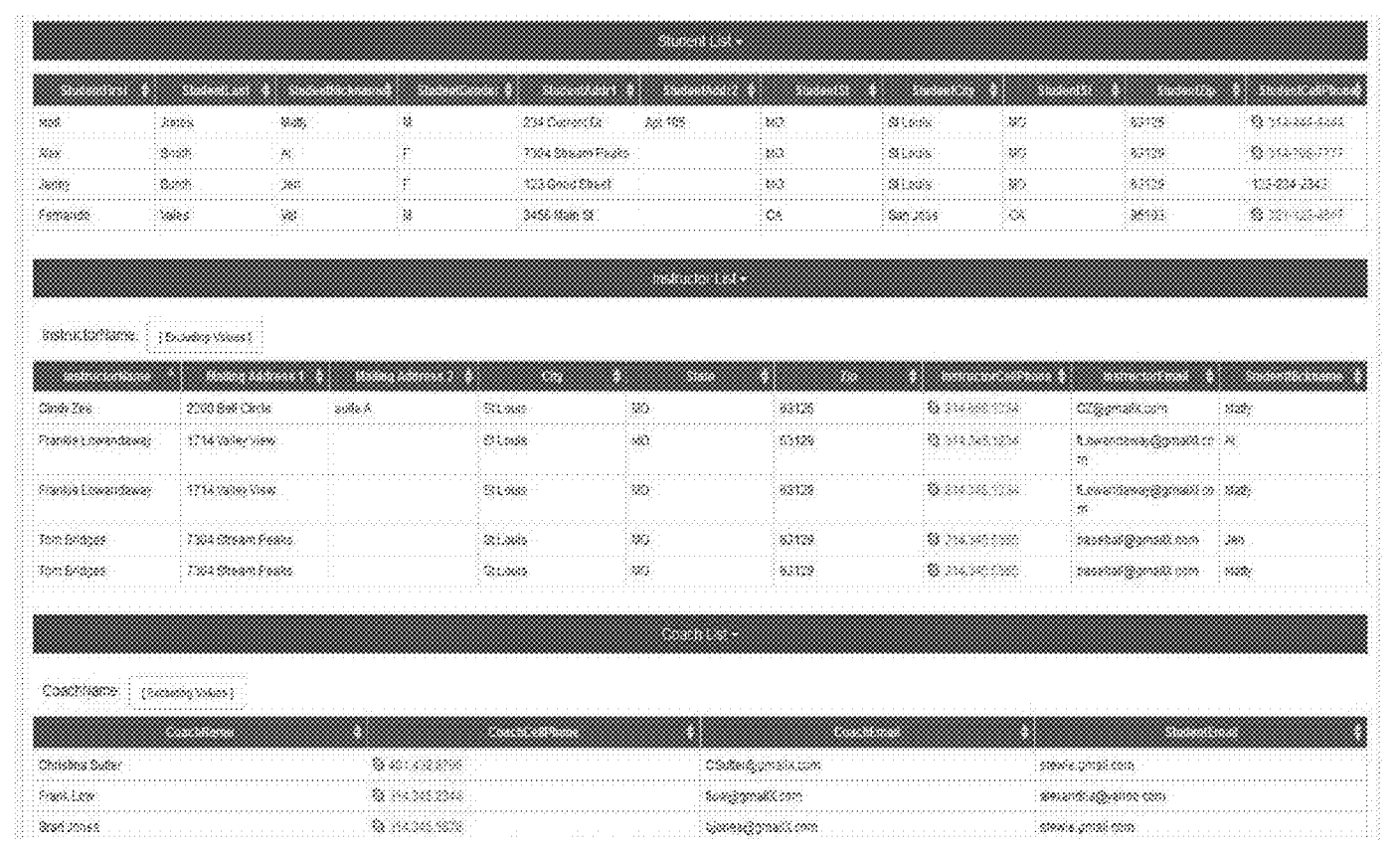

With respect to FIG. 18, an example of multiple User Records is shown. In this embodiment, the system may display the User Records according to Personal Information 602 and Status/Relationships Information 604. For example, for the record associated with student Matt, his personal information may be shown. In addition, the personal information from the records of his coaches and instructors may be shown. Another example of this is shown in FIG. 19, except in this example a group of students and their personal information may be displayed in connection with the personal information of instructors and coaches. Such a view may be displayed for example when a coach record is selected, rather than a student record.

Figure 20:
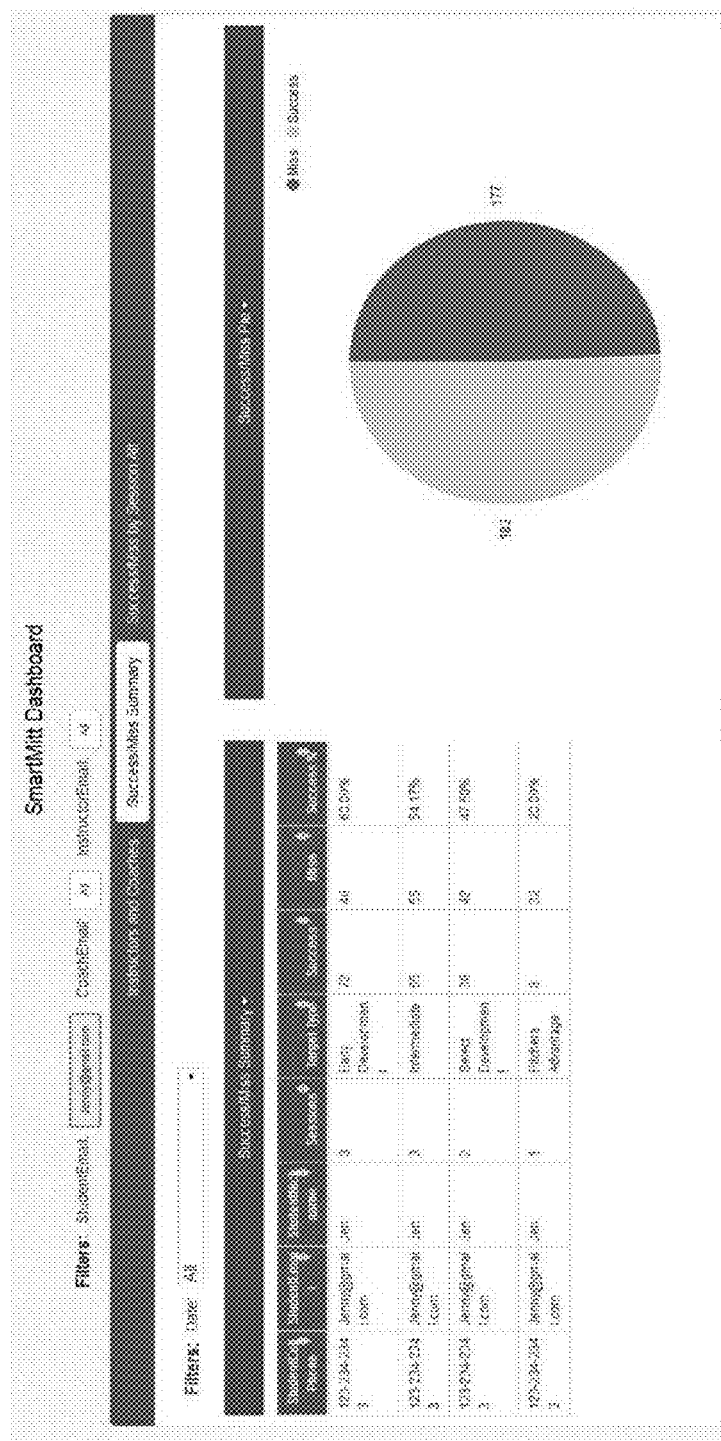
FIG. 20 illustrates an example of performance/analytics information for a particular user.

With respect to FIG. 20, an example of performance/analytics information is shown for a particular user. As shown in the example, the user record is for a student who has used four different Target Data Templates (Early Development, Intermediate, Select Development, Pitchers Advantage). Based on the user's record of hitting the target areas according to the Target Data in the User Record, a cumulative score of hits and misses can be calculated. In some embodiments, other parameters may be calculated from the Target Data, such as hit, near hit, and total miss.

Figure 21:
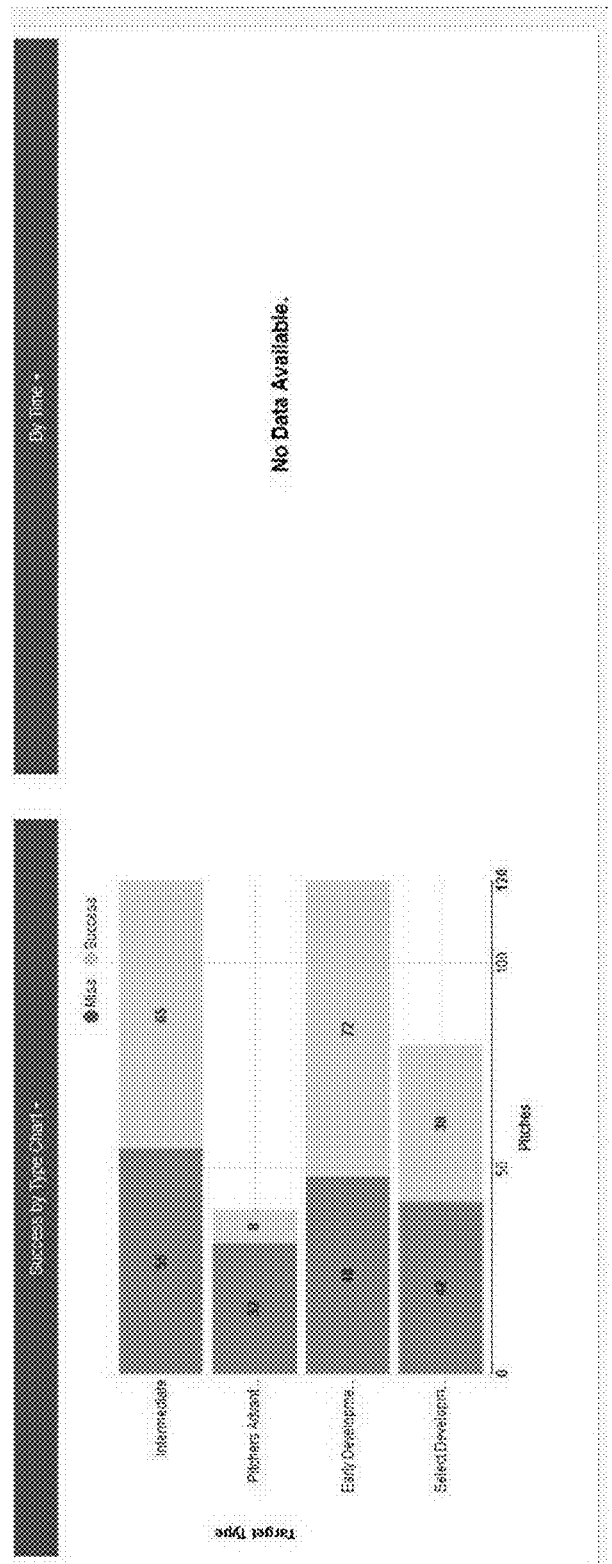
FIG. 21 illustrates another example of performance/analytics information for a particular user.
Figure 22:
FIG. 22 illustrates another example of performance/analytics information for a particular user.

With respect to FIG. 21, another example of performance/analytics information is shown for a particular user. In this example, Target Data from different sessions (e.g., on different days) may be graphed over time to show improvement or lack thereof. For example, after every pitching session with a specific Target Data Template, a hit/miss ratio may be calculated as shown in FIG. 22. These hit/miss ratios may then be shown over time, such as on a daily, weekly, or monthly basis, to show whether the user is improving or not.

Figure 23:
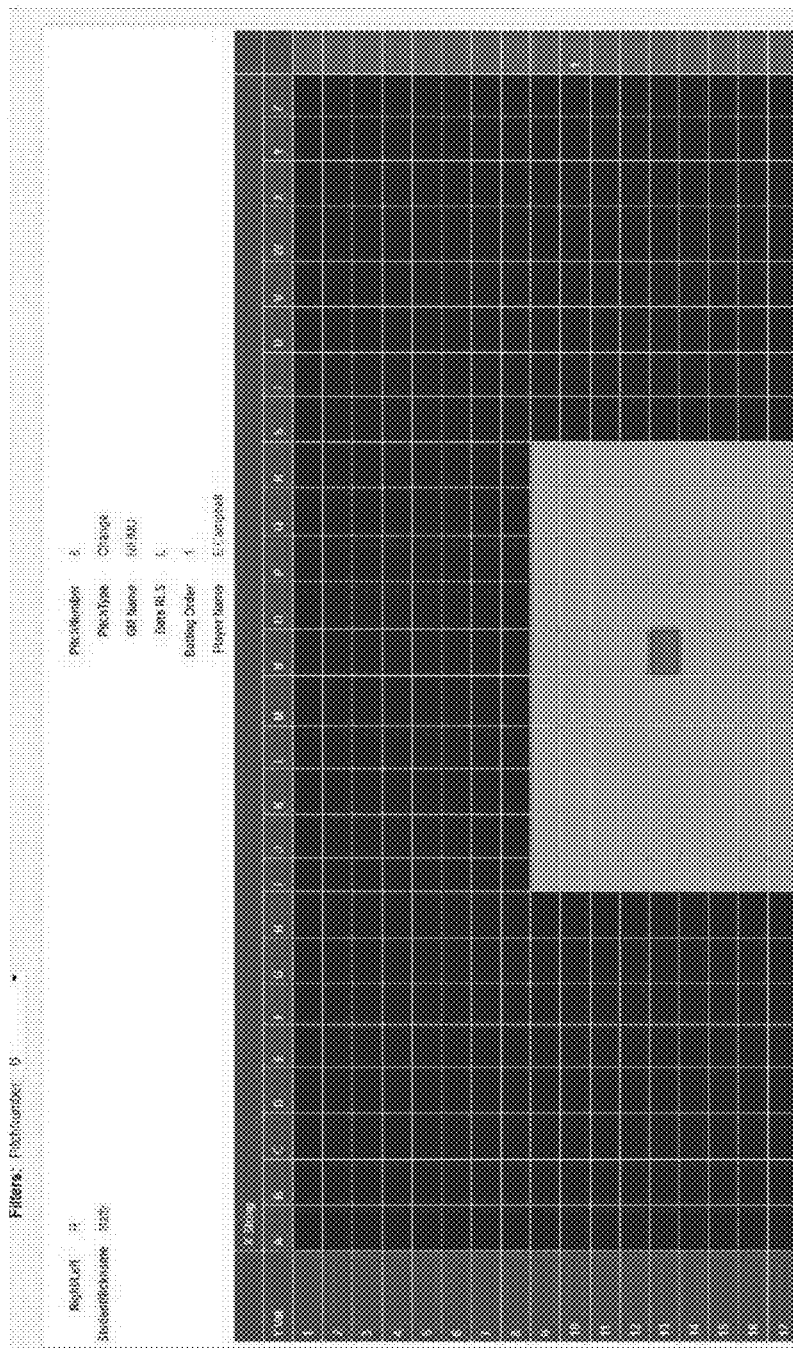
FIG. 23 illustrates an example of how a target data template may be constructed to form a game mode.
Figure 24:
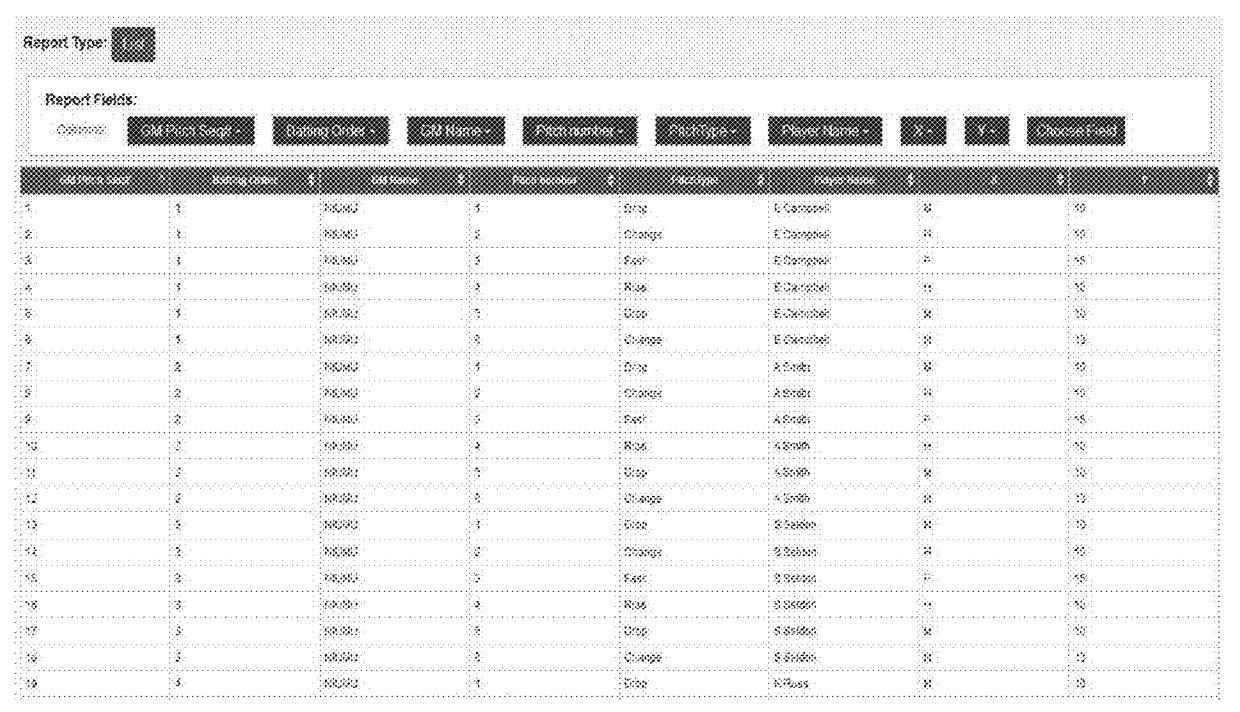

With respect to FIG. 23, an example is shown of how a Target Data Template may be constructed to form a Game Mode. In a Game Mode, a user may create a sequence of Data Templates corresponding to a particular pattern of throwing or hitting of an object that is desired. For example, baseball has an established lineup of batters, each of which may have an optimal strike zone that differs from one player to the next. A coach therefore may want to create a Game Mode that shows where the pitcher should throw from one batter to the next. As shown in FIG. 23, an optimal target within the strike zone is shown for the batter Matty as indicated by the dark spot within the strike zone. In addition, other information may be associated with the Target Data Template to help a user understand the particular target. For example, a Target Data Template in a Game Mode created for a batter may include her position in the lineup, batting stance, preferred pitch type, etc. An example of this is also shown in FIG. 24. This additional information may also be presented to the user via the Target Display or may be omitted.

A Game Mode may also include rules or conditions to help simulate realistic play. For example, depending on where a pitch is determined to hit on a Target Data Template, probabilities may be used to determine the result of the pitch (e.g., home run, player advances to first, pop-fly caught, ball, strike). Accordingly, the Game Mode may be used to simulate the effect of a game (e.g., 2 strikes, 4 balls, player walks, change to next Target Data Template) by using rules of probability to simulate a game based on the athlete's performance.

In addition, the Game Mode may be used to simulate the performance of a rival team pitcher based on another user's record. For example, once a pitcher strikes out three batters, he or she may rest while watching a simulation of how another user would perform against Target Data Templates representing batters on his or her own team. In such embodiments, the system may determine a probability of where a rival user may hit on the Target Data Templates and use that to simulate outcomes. Alternatively, as another example, two pitchers may compete against each other using two sets of Target Data Templates to represent their teams, until a game is over.

As another example of a Game Mode, the system may use probabilistic algorithms or patterns to create dynamic Target Data Templates. For example, the Game Mode may display a wandering target within a strike zone with a dynamic Target Data Template. The more frequently the pitcher hits the target, the faster the wandering target may move.

In another embodiment, a Game Mode may use Target Data Templates where each Target Data Template specifies information and instructions relevant to the throwing or hitting of an object. For example, a Target Data Template may contain information relating to a virtual player, such as whether the virtual player is left-handed or right-handed, and the optimal type of pitch(es) (e.g., fastball, curveball, screwball, changeup, drop) that should be thrown against such a virtual player. The system may then allow for Target Data Templates to be organized according to sequence based on a group of virtual players, where each virtual player is assigned to a subset of Target Data Templates. For example, the Game Mode may present a batting order, where subsets of Target Data Templates are presented in accordance with the batting order. In Game Mode, the system may then randomly or deterministically select Target Data Templates associated with a particular batter until either the batter is struck out or the Game Mode determines a different outcome based on failed pitches. For example, if a pitch is not delivered correctly, the Game Mode may determine that a hit, strike, bunt, foul tip, home run, etc. may have occurred. In this manner, the Game Mode may progress as if simulating an actual game. Further, such simulation may be based on statistical models of each virtual player that are based on the past or predicted performance of a real athlete. For instance, the Game Mode may determine there is a 25% chance that a ball with a particular speed that hits a particular location may result in a home run based on such statistical models of a real athlete. In some embodiments, even if the pitch is delivered correctly, the Game Mode may still determine an outcome based on a statistical model, thereby possibly increasing a sense of realism for an athlete.

As described above, Target Data Templates may be used by the system to present the information relating to a virtual player (e.g., Left-Handed/Fastball) and may also present particular locations where an object, such as a baseball, should hit.

In some embodiments, a Game Mode may save the results from such a sequence of practice and also may perform statistical analysis. For example, the Game Mode may determine success ratios based on particular information relating to virtual players (e.g., success rate against left-handed batters). As another example, the Game Mode may determine success after a transition has occurred (e.g., success rate against a left-handed batter following a right-handed batter). Such results and statistical analysis may then be used by athletes or coaches to determine particular weaknesses, such as difficulties in throwing to a particular location, a particular type of pitch, transitioning from one situation to another, etc.

While particular embodiments and applications of the present invention have been illustrated and described, it is to be understood that the invention is not limited to the precise construction and compositions disclosed herein and that various modifications, changes, and variations can be apparent from the foregoing descriptions without departing from the spirit and scope of the invention as defined in the appended claims.

What is claimed is:

1. A system for monitoring objects thrown or hit by an athlete comprising:
   an electronic display, wherein the electronic display contains an arrangement of light-emitting devices for displaying targets to the athlete;
   one or more cameras, wherein at least one camera is positioned to observed the electronic display; and
   a computer coupled to the electronic display and the one or more cameras, wherein the computer uses video from the one or more cameras to determine relative to the electronic display where an object is thrown or hit.

2. The system of claim 1, wherein the computer further determines the trajectory of the object based on a frame-by-frame analysis of the video.

3. The system of claim 2, wherein the computer further determines a termination point of a thrown or hit object based on an abrupt change in the trajectory of the object.

4. The system of claim 3, wherein the computer further determines whether the termination point corresponds to a portion of an electronic display.

5. The system of claim 4, wherein determining whether the termination point corresponds to a portion of an electronic display is based on a visually distinct area presented by the electronic display that is observed by the one or more cameras.

6. The system of claim 5, wherein the electronic display is composed of an array of light-emitting diodes that are visually distinct due to the physical separation existing between the light-emitting diodes.

7. The system of claim 5, wherein the electronic display uses color and light intensity to form visually distinct areas.

8. A computer operable method for monitoring objects thrown or hit by an athlete comprising:

observing an electronic display, wherein the electronic display contains an arrangement of light-emitting devices for displaying targets to the athlete, via one or more cameras, wherein at least one camera is positioned to observe the electronic display; and using video from the one or more cameras to determine relative to the electronic display where an object is thrown or hit.

9. The computer operable method of claim 8, further comprising the step of determining the trajectory of the object based on a frame-by-frame analysis of the video.

10. The computer operable method of claim 9, further comprising the step of determining a termination point of a thrown or hit object based on an abrupt change in the trajectory of the object.

11. The computer operable method of claim 10, further comprising the step of determining whether the termination point corresponds to a portion of an electronic display.

12. The computer operable method of claim 11, wherein determining whether the termination point corresponds to a portion of an electronic display is based on a visually distinct area presented by the electronic display that is observed by the one or more cameras.

13. The computer operable method of claim 12, further comprising the step of using color and light intensity on the electronic display to form visually distinct areas.

14. The computer operable method of claim 8, wherein each light-emitting device of the arrangement of light-emitting devices is in a stationary position during video recording.

15. The system of claim 1, further comprising one or more transparent barriers to protect the arrangement of light-emitting devices from damage by a thrown or hit object.

16. The system of claim 15, wherein the one or more transparent barriers is comprised of one or more catching nets.

17. The system of claim 1, wherein each light-emitting device of the arrangement of light-emitting devices is in a stationary position during video recording.

18. The system of claim 1, wherein the arrangement of light-emitting devices is in a grid-like arrangement.

19. The system of claim 1, wherein the computer is further configured to display text or graphics via the electronic display.

20. The system of claim 1, wherein the computer is further configured to determine the rotations of an object based on a frame-by-frame analysis of the video and the positioning of one or more visual indicators on said object within each video frame.

* * * * *